(12) United States Patent
Kazic et al.

(10) Patent No.: US 9,610,125 B2
(45) Date of Patent: Apr. 4, 2017

(54) LASER SYSTEM AND METHOD FOR THE TREATMENT OF BODY TISSUE

(71) Applicant: Fotona d.d., Ljubljana (SI)

(72) Inventors: Marko Kazic, Dob (SI); Matjaz Lukac, Ljubljana (SI)

(73) Assignee: Fotona D.O.O., Ljubljana (SI)

( * ) Notice: Subject to any disclaimer, the term of this patent is extended or adjusted under 35 U.S.C. 154(b) by 322 days.

(21) Appl. No.: 14/316,925

(22) Filed: Jun. 27, 2014

(65) Prior Publication Data
US 2015/0005755 A1    Jan. 1, 2015

(30) Foreign Application Priority Data

Jun. 27, 2013 (EP) ..................................... 13003273

(51) Int. Cl.
*A61B 18/20* (2006.01)
*A61B 18/22* (2006.01)
*A61N 5/06* (2006.01)

(52) U.S. Cl.
CPC .............. *A61B 18/20* (2013.01); *A61B 18/22* (2013.01); *A61B 2018/2085* (2013.01); *A61B 2018/2095* (2013.01); *A61B 2018/2277* (2013.01); *A61N 5/0603* (2013.01); *A61N 2005/0644* (2013.01); *A61N 2005/0659* (2013.01)

(58) Field of Classification Search
CPC .. A61F 9/008; A61F 9/00802; A61F 9/00821; A61F 2009/00897; A61B 18/18; A61B 18/20; A61B 18/22; A61B 2018/00327; A61B 2018/00505; A61B 2018/00517; A61B 2018/00559; A61B 2018/00571; A61B 2018/00577

USPC .......... 606/10–14; 607/134–138; 433/29–31; 128/898
See application file for complete search history.

(56) References Cited

U.S. PATENT DOCUMENTS 5,486,171 A * 1/1996 Chou .................... A61B 18/24
606/11
5,496,307 A * 3/1996 Daikuzono ............ A61B 18/24
606/15

(Continued)

FOREIGN PATENT DOCUMENTS

| WO | 2008/057154 A2 | 5/2008 |
| WO | 2011/010246 A1 | 1/2011 |
| WO | 2012/037954 A1 | 3/2012 |

*Primary Examiner* — Ahmed Farah
(74) *Attorney, Agent, or Firm* — Gudren E. Huckett (57) ABSTRACT

A laser system for body tissue treatment has laser source, control device, scanner, and handpiece with treatment head transparent to the laser beam. An incoming laser beam section enters the treatment head longitudinally. The treatment head has a conical output surface with a minimum and a maximum surface radius and a half opening angle for total reflection of the incoming beam section. The reflected beam section is refracted radially into an emerging beam section away from the treatment head through the output surface. The incoming beam section has at the output surface a mean diameter that is ≤a difference of maximum surface radius and minimum scanning radius. A conical scanning surface as a part of the conical output surface extends from the minimum scanning radius to the maximum surface radius. The control device controls the scanner for scanning the conical scanning surface with the incoming beam section.

18 Claims, 3 Drawing Sheets

(56) References Cited

U.S. PATENT DOCUMENTS

| | | | | |
|---|---|---|---|---|
| 5,833,683 A | * | 11/1998 | Fuller | A61B 18/22 606/17 |
| 6,102,905 A | * | 8/2000 | Baxter | A61L 2/10 606/15 |
| 6,942,658 B1 | * | 9/2005 | Rizoiu | A61B 18/22 606/16 |
| 7,697,814 B2 | * | 4/2010 | Rizoiu | A61B 18/22 362/298 |
| 2013/0190738 A1 | * | 7/2013 | Lukac | A61B 18/20 606/10 |

* cited by examiner

LASER SYSTEM AND METHOD FOR THE TREATMENT OF BODY TISSUE

BACKGROUND OF THE INVENTION

The present invention relates to a laser system for the treatment of body tissue on an inner circumferential tissue surface and to a related method.

Various laser wavelengths, which are highly absorbed in water, such as Er:YAG (2.94 μm wavelength), Er,Cr:YSGG (2.73 μm wavelength), $CO_2$ (8-11 μm wavelength) have been advocated as possible and promising alternatives to conventional instruments in different medical and surgical disciplines. Due to their characteristic absorption maxima in water which is an important constituent of body tissues, they are considered to be suitable not only for the treatment of soft tissue structures but also for ablating mineralized hard tissues. Contact-free laser ablation offers the opportunity of cutting bone and other hard tissue without friction that may cause additional thermal and mechanical trauma. Consequently, the risk of cell death and delayed healing may be minimized. Furthermore, in contrast to conventional procedures, no tissue particles debris is left on the tissue surface leading to a smear layer on the treated surface. This is due to the laser tissue ablation mechanism. Absorption and the following transformation of laser irradiation into heat result in a rapid phase change which, in turn, creates internal pressures, causing micro-fracturing and micro-explosive removal of the mineral phase of the hard tissues. Besides, during the laser ablation of the tissue, the vaporization of water leads to a fast removal of the tissue layers. The result is an extremely clean and micro-structured tissue surface without thermal damage and smear layer, resulting in reduced inflammatory response and accelerated tissue regeneration and attachment. This is, for example, important in implantology where faster attachment of the bone to the inserted implants is crucial for faster patient recovery time.

Nevertheless, drawbacks of hard tissue laser surgery such as a considerable amount of time needed, lack of depth control, and highly sophisticated handling requirements are still formidable. An advantage of mechanical tools such as drills and saws is that the surgeon has a very good tactile contact with the treated tissue providing feedback to the surgeon regarding the speed of the procedure and the depth of the drilled hole or cut. For this reason, laser bone cutting is still assessed to be inferior to many conventional as well as other methods, such as piezoelectric osteotomy. In particular, when creating a hole in hard body tissue like bone material, mechanical tools are commonly still preferred. This preference however leaves unanswered the question of how to handle the aforementioned issues like e.g. residual smear layers on the inner circumferential body tissue surface of said hole. The treatment results of the inner circumferential body tissue surface by mechanical means are unsatisfactory. The same applies to soft tissue treatment on inner circumferential body surfaces as performed e.g. in vaginal or anal treatments. It is therefore desirable to develop means to treat circumferential body tissue surfaces with a laser.

One possible solution for treating circumferential body tissue surfaces involves a laser system comprising of a laser source for the generation of a laser beam and a handpiece with a special reflection mirror treatment head, as disclosed in WO 2012/037954 A1. The laser system comprises a laser source for generating a laser beam and a handpiece with a treatment head. The treatment head extends along a longitudinal axis and is adapted in a manner such that the longitudinal axis of the treatment head during operation is at least approximately parallel to the inner circumferential tissue surface. During operation, the laser beam enters the treatment head in the direction of the longitudinal axis. A reflection mirror with a conical shape is disposed in the treatment head and guides the laser beam radially outwards out of the treatment head onto the inner circumferential tissue surface. Movable deflection means for the laser beam are provided to scan the inner circumferential tissue surface within a treatment area at least in a circumferential direction. One drawback of this solution is that the treatment head must consist of mechanical means for holding the conical reflection mirror in the proper position, making the design and manufacture of such treatment head relatively difficult. Another drawback of this solution is that the reflected beam gets spread out not only in the transverse direction, due to the circular shape of the treatment head, but also in the longitudinal direction due to the varying radius of the cone in the longitudinal direction.

Another option for treating circumferential body tissue surfaces with a laser is to use a fiber tip with a conical end. Using this solution, the fiber tip is positioned at least approximately parallel to the inner circumferential tissue surface. The laser beam is guided within the fiber tip dimensions in such a manner that the beam extends substantially over the whole cross section of the fiber tip. Because of the conical end of the tip, the beam, before exiting the tip, is at least partially reflected on the conical tip surface, resulting in the exiting beam being at least partially guided radially outwards out of the fiber tip and unto the inner cavity circumferential tissue surface. This solution is mechanically less complex than the solution with the reflection mirror treatment head. However, it is unsatisfactory when high power densities are required to treat or modify the tissue. Since the energy of the beam is distributed over the whole circumference of the body cavity, the resulting laser power density (in $W/cm^2$) is significantly reduced. For this reason, the conical fiber tip technique is unsuitable for treating larger diameter cavities, where the reduction in laser power density is most pronounced. Another drawback of this solution is that the body tissue is being treated indiscriminately over the whole circumference of the cavity. In some medical procedures, it is desirable that certain areas of the cavity remain untreated, or treated with a different energy. For example, in gynecological treatments, it may be desirable to avoid a laser irradiation of the urethra. A third drawback of this solution is that the laser beam impacts also on the sharp apex of the conical surface. It is technologically challenging, if not impossible, to manufacture a perfect apex. In addition, at high laser intensities, and with continued use, it is this apex that becomes damaged first. For this reason, the part of the beam which impinges on the apex becomes at least partially transmitted also in the forward (longitudinal) direction, possibly damaging the tissue at the bottom of the treated cavity.

The invention has the object to provide an improved laser system which allows treating circumferential body tissue surfaces of large diameters.

SUMMARY OF THE INVENTION

This object is solved by a laser system for the treatment of body tissue on an inner circumferential tissue surface, comprising a laser source for the generation of a laser beam, a handpiece with a treatment head, a control device, and a scanner, wherein the treatment head extends along a longitudinal axis and is made of a material which is transparent to the laser beam and which has a first refractive index, wherein, during operation, an incoming beam section of the laser beam enters the treatment head in the direction of the longitudinal axis, wherein the treatment head has a conically shaped output surface being disposed around the longitudinal axis and having an apex facing away from an origin of the incoming beam section, wherein the conically shaped output surface has a minimum surface radius (r) and a maximum surface radius (R), wherein the conically shaped output surface has a half opening angle (α) being adapted to provide total reflection of the incoming beam section into a reflected beam section within the treatment head and to provide refraction of the reflected beam section into an emerging beam section emerging radially from the treatment head through the output surface, wherein, from the minimum surface radius (r) and the half opening angle (α), a minimum scanning radius ($R_{in}$) is derived according to:

$$R_{in}=r(tg(2\alpha)+tg(\alpha))/(tg(2\alpha)-tg(\alpha)),$$

wherein the incoming beam section has at the location of the output surface a mean diameter (d) being ≤the difference of the maximum surface radius (R) and the minimum scanning radius ($R_{in}$), wherein, as a part of the conically shaped output surface, a conically shaped scanning surface is defined extending from the minimum scanning radius ($R_{in}$) to the maximum surface radius (R), wherein the control device is adapted to control the scanner for scanning at least a portion of the conically shaped scanning surface with the incoming beam section.

The invention further has the object to provide an improved method for treating circumferential body tissue surfaces of large diameters.

This object is solved by a method for operating a laser system for the treatment of body tissue on an inner circumferential tissue surface, wherein the laser system comprises a laser source for the generation of a laser beam, a handpiece with a treatment head, a control device, and a scanner, wherein the treatment head extends along a longitudinal axis and is made of a material which is transparent to the laser beam and which has a first refractive index, wherein, during operation, an incoming beam section of the laser beam enters the treatment head in the direction of the longitudinal axis, wherein the treatment head has a conically shaped output surface being disposed around the longitudinal axis and having an apex facing away from an origin of the incoming beam section, wherein the conically shaped output surface has a minimum surface radius (r) and a maximum surface radius (R), wherein the conically shaped output surface has a half opening angle (α) being adapted to provide total reflection of the incoming beam section into a reflected beam section within the treatment head and to provide refraction of the reflected beam section into an emerging beam section emerging radially from the treatment head through the output surface, wherein, from the minimum surface radius (r) and the half opening angle (α), a minimum scanning radius ($R_{in}$) is derived according to:

$$R_{in}=r(tg(2\alpha)+tg(\alpha))/(tg(2\alpha)-tg(\alpha)),$$

wherein the incoming beam section has at the location of the output surface a mean diameter (d) being ≤the difference of the maximum surface radius (R) and the minimum scanning radius ($R_{in}$), wherein, as a part of the conically shaped output surface, a conically shaped scanning surface is defined extending from the minimum scanning radius ($R_{in}$) to the maximum surface radius (R), wherein the scanner is controlled by the control device such that at least a portion of the conically shaped scanning surface is scanned with the incoming beam section, wherein the incoming beam section is subjected at the conically shaped scanning surface to total reflection into a reflected, beam section within the treatment head, and wherein the reflected beam section is refracted at the conically shaped output surface into an emerging beam section radially emerging from the treatment head through the output surface, wherein during operation of the laser system the treatment head is positioned with its longitudinal axis at least approximately parallel to the inner circumferential tissue surface, and wherein the inner circumferential tissue surface is at least partially scanned by the emerging beam section.

In the following, the expressions "treatment" or "to treat" will be used in a broad sense, meaning not only the treatment in a medical sense but also tissue stimulation, and as well ablation and coagulation of the tissue.

According to the invention, the laser system comprises a laser source for the generation of a laser beam, a handpiece with a treatment head, a control device, and a scanner, wherein the treatment head extends along a longitudinal axis and is made of a material which is transparent to the laser beam and which has a first refractive index, wherein, during operation, an incoming beam section of the laser beam enters the treatment head in the direction of the longitudinal axis, wherein the treatment head has a conically shaped output surface being disposed around the longitudinal axis and having an apex facing away from an origin of the incoming beam section, wherein the conically shaped output surface has a minimum surface radius and a maximum surface radius, wherein the conically shaped output surface has a half opening angle being adapted to provide total reflection of the incoming beam section into a reflected beam section within the treatment head and to provide refraction of the reflected beam section into an emerging beam section emerging from the treatment head through the output surface in a radial direction relative to the longitudinal axis. From the minimum surface radius and the half opening angle a minimum scanning radius is derived according to the equation 1 mentioned below. The incoming beam section has at the location of the output surface a mean diameter being ≤the difference of the maximum surface radius and the minimum scanning radius. As a part of the conically shaped output surface, a conically shaped scanning surface is defined that extends from the minimum scanning radius to the maximum surface radius. The control device is adapted to control the scanner for scanning at least a portion of the conically shaped scanning surface with the incoming beam section.

In the related method, the scanner is controlled by the control device such that at least a portion of the conically shaped scanning surface is scanned with the incoming beam section, that the incoming beam section, at the conically shaped output surface, is subjected to total reflection into a reflected beam section within the treatment head, and that the reflected beam section is refracted at the conically shaped output surface into an emerging beam section emerging from the treatment head through the output surface in a radial direction relative to the longitudinal axis, wherein during operation of the laser system the treatment head is positioned with its longitudinal axis at least approximately parallel to the inner circumferential tissue surface, and wherein the inner circumferential tissue surface is at least partially scanned by the emerging beam section.

In any case, the scanning pattern and the beam diameter must be adjusted such that the apex or the bottom of the treatment head, if present, are entirely excluded from irradiation in order to prevent the beam to be at least partially transmitted also in the forward (longitudinal) direction, possibly damaging the tissue at the bottom of the treated cavity.

The scanning area that fulfils this condition is limited to a ring shaped area, defined by an outer ring radius which is equal to the maximum surface radius R, and an inner ring radius $R_{in}$ which can be mathematically calculated with equation 1 (Eq. 1):

$$R_{in}=r(tg(2\alpha)+tg(\alpha))/(tg(2\alpha)-tg(\alpha)) \qquad \text{(Eq. 1)}$$

Here, $\alpha$ is the half-opening angle of the conically shaped output surface, and r is its minimum surface radius. In order to fit into the above ring-shaped permissible scanning area, the laser beam diameter d must therefore fulfill $d \leq R-R_{in}$. This is of course possible and realizable only when the treatment head's maximum surface radius R is >the inner ring radius $R_{in}$. As an example, for an angle $\alpha=36°$, the inner radius of the permissible scanning area ring is equal to $R_{in}=1.6$ r, and the beam diameter is limited to $d \leq R-1.6$ r.

According to the invention, the optical element has a diameter substantially larger than the diameter of the laser beam, resulting in the laser beam propagating freely within the optical element. The inventive device and method allow for accessing tissue surfaces which are not easily accessible and which exist in the inner side of a hole or a body opening. The treatment head of the handpiece may be axially inserted into the hole or into the body opening. The treatment head is of low complexity, but nevertheless allows for a treatment of the circumferential tissue surface in any desired scanning pattern.

The invention is particularly suitable for treating large diameter body cavities (such as, for example, a vagina) or modifying surfaces of surgically made holes in human hard tissues (such as in implantology). The invention also avoids the beam being transmitted in a forward direction through the imperfectly manufactured and/or damaged conical fiber's apex. It also allows selective treatment since the scanner can be programmed to skip or undertreat certain parts of the tissue surface. It is to be appreciated that when treating deeper cavities, the treatment of the cavity might have to be accomplished by not only moving the beam across the treatment head but also by moving the treatment head either manually or by using an electronically controlled and movable device, up and/or down along the cavity's length, in order to treat the circumferential surface along the cavity's length.

The inventive laser system is in particular suitable for post treatment when drilling holes in hard bone material, e.g. in implantology. At first, the hole is mechanically produced (drilled) as usual. Subsequently the laser system is used as a laser grater or laser rasp, by means of which residual smear layers of loose bone material are cleared from the inner circumferential tissue surface of the drilled hole. In addition, the drilled hole may be brought to its nominal measure with improved precision. Finally, it is possible to achieve a desired surface quality and even a desired surface structuring. In addition to the treatment of hard bone material the inventive laser system is suitable for the treatment of soft body tissue like skin or the like, in particular for vaginal, urinal, rectal, or ENT (ear, nose and throat) treatments.

Another important advantage of the invention is that the laser system can be electronically controlled to adjust the scanning pattern and/or laser energy depending on the position of the beam on the circumferential surface of the body cavity. For example, in gynecological treatments, the scanner can be programmed not to scan the beam over the urethra. Alternatively, the laser intensity can be reduced or turned off when the beam is being scanned over the urethra.

The treatment head is made out of a material which is optically transparent (i.e. substantially non-absorbing) at the laser wavelength used for treatment. "Substantially non-absorbing material" means a material with a laser beam transmission within the treatment head beam path length that is above 80%. Preferably, the treatment head base body is of a cylindrical shape. However, any other suitable 3D shape, such as a cube, cuboid, hexagonal prism or a cone, can be used, provided that the shape terminates in a conically shaped output surface.

An important advantage of the invention as compared to the aforementioned reflecting conical mirror approach is that due to the fact that the beam interacts with the conical output surface twice (firstly by total reflection and secondly by a subsequent refraction), the dispersion in the longitudinal direction is subtracted out, and the beam is spread out only in a transverse direction, with the spot on the treated tissue having an elliptical shape.

Any radial emerging direction of the emerging beam section having a radial direction component relative to the treatment head's longitudinal axis might be desirable within the scope of the present invention.

However, the following inventive considerations lead to further improvements: The half opening angle $\alpha$ must be equal to or smaller than the critical angle $\alpha_{cr}$ required for the total internal reflection to occur. This ensures that the incoming beam is totally reflected at first contact with the conical surface, and does not exit the treatment head in a substantially longitudinal direction. The condition for the total reflection can be mathematically calculated with equation 2 (Eq. 2):

$$\alpha < \alpha_{crit} = 90° - \arcsin(n_2/n_1) \qquad \text{(Eq. 2)}$$

Here, $n_1$ is the index of refraction of the treatment head's optical material and $n_2$ is the index of refraction of the material surrounding the treatment head's conical ending. This material may be air, externally supplied liquids such as water or acid, or internally generated bodily fluids such as blood.

While any angle $\alpha$ smaller than $\alpha_{crit}$ is acceptable from the viewpoint of the total reflection, it is desirable to keep its value as close to $\alpha_{crit}$ as possible. Namely, as the angle $\alpha$ becomes smaller, the reflected light becomes more concentrated in the small volume around the sharp conical ending of the treatment head. This results in a high laser power density, increasing the likelihood of the optical damage of the treatment head.

It is also desirable that the angle $\alpha$ is such that when the beam is refracted out of the cone, it exits the treatment head at substantially 90 degrees to the treatment head's longitudinal axis. This ensures that the beam is directed perpendicularly to the circumferential surface of the cavity, resulting in the largest possible laser power density on the treated surface. The optimal angle $\alpha_{opt}$ for which this condition is fulfilled, can be mathematically calculated with equation 3 (Eq. 3):

$$(n_2 \sin \alpha_{opt})/(n_1 \cos 3\alpha_{opt})=-1 \qquad \text{(Eq. 3)}$$

It is important to note that depending on the particular combination of $n_1$ and $n_2$ the optimal angle, $\alpha_{opt}$ is not necessarily smaller than $\alpha_{crit}$. In such case no total reflection would occur. Therefore, the treatment head functions optimally only under the condition, that the combination of refractive indexes $n_1$ and $n_2$ support both conditions expressed by Eqs. 2 and 3.

Derived from the aforementioned inventive considerations, and in a preferred embodiment of the invention, the treatment head is made of a material having a first refractive index of >1.28, while, from the first refractive index of the treatment head material and a second refractive index of air, an optimal half opening angle $\alpha_{opt}$ of the conically shaped output surface is derived according to the above mentioned Eq. 3, and the half opening angle $\alpha$ of the conically shaped output surface is at least approximately equal to the optimal half opening angle $\alpha_{opt}$. By choosing said material having a first refractive index of >1.28 at least for operation of the treatment head immersed in air, both requirements of Eqs. 1 and 2 can be met, resulting in a) the incoming beam section being totally reflected and b) the reflected beam section subsequently refracted such that the emerging beam section emerges from the treatment head at least approximately at an angle $\beta$ of approximately 90° with respect to the treatment head's longitudinal axis and also at approximately 90° with respect to the cavity's circumferential tissue surface. "Approximately 90°" does mean in the present context a 90° angle with a tolerance of ±10°, preferably with a tolerance of ±3°.

In a preferred embodiment, the treatment head is covered by a liquid-tight protective sleeve made of a material being transparent to the laser beam, wherein the conically shaped output surface is surrounded by a circumferential wall of the protective sleeve, and wherein a free space between the conically shaped output surface and the circumferential wall is filled with gas, preferably with air. This allows for a treatment head's use under any conditions, regardless of whether air or any liquid like water or blood is present at the treatment site. The protective sleeve protects the conically shaped output surface from becoming soiled by any such media, i.e., keeps the output surface clean, thereby reliably maintaining the conditions for total reflection and subsequent refraction.

However, under certain circumstances, the invention will work as well when the treatment head is adapted for immediate access to the body tissue on the inner circumferential tissue surface. This is based on the following inventive considerations:

Table 1 shows calculated critical and optimal angles for three different optical materials, YAG ($n_1$=1.8), quartz ($n_1$=1.5) and CaF$_2$ ($n_1$=1.4), of the treatment head, and three different surrounding media, air ($n_2$=1.0), water ($n_2$=1.3), and blood ($n_2$=1.4), within the cavity. The calculations are made only for the purposes of describing the invention. The values for the indexes of refraction, $n_1$ and $n_2$, and the calculated angles are therefore only approximate. The exact values of the indexes of refraction $n_1$ and $n_2$ and therefore of the calculated angles will depend also on the laser wavelength, manufacturer of the material, temperature etc. Note also that there are many other optical materials available, and that many other surrounding media can be present during cavity treatments, such as for example, disinfecting or sterilizing liquids (alcohol, acid . . . ).

TABLE 1

Calculated critical and optimal angles

| Treatment Head | External Media | Critical Angle $\alpha_{crit}$ | Optimal Angle $\alpha_{opt}$ |
|---|---|---|---|
| YAG ($n_1$ = 1.8) | Air ($n_2$ = 1.0) | 56° | 36° |
| | Water ($n_2$ = 1.3) | 44° | 39° |
| | Blood ($n_2$ = 1.4) | 39° | 40° |
| Quartz ($n_1$ = 1.5) | Air ($n_2$ = 1.0) | 48° | 38° |
| | Water ($n_2$ = 1.3) | 30° | 42° |
| | Blood ($n_2$ = 1.4) | 21° | 43° |
| CaF$_2$ ($n_1$ = 1.4) | Air ($n_2$ = 1.0) | 45° | 39° |
| | Water ($n_2$ = 1.3) | 24° | 43° |
| | Blood ($n_2$ = 1.4) | 10° | 45° |

The data shown in Table 1 are first discussed assuming that the treatment is carried out with a wavelength which is not strongly absorbed in water or air, such as, for example, an Nd:YAG laser wavelength of 1064 nm.

In the case of YAG crystal, with relatively high index of refraction, the data in Table 1 demonstrates that a treatment head can be perfectly designed at an optimal angle for situations when the surrounding media are air or water. This is due to the fact that the optimal angles under these two conditions are smaller than the corresponding critical angles, thus satisfying the condition for total internal reflection. This does not strictly apply in the case of blood. However, even in the case of blood, the critical and optimal angles do not differ significantly. Thus, by designing a treatment head to have the conical angle $\alpha$ slightly smaller than the critical angle for blood of 39°, the laser beam would be totally reflected and then refracted out of the treatment head in a substantially perpendicular, or close to perpendicular, direction with regard to the treatment surface, independently of the type of the surrounding media. This is important when the treatment head must be functional regardless of whether the cavity is initially dry at the beginning of the treatment and becomes filled with water or blood only at a later stage of the treatment. It may also be that the quantity of water and/or blood within the cavity varies and/or fluctuates uncontrollably (for example under the influence of externally supplied pressurized air): this emphasizes the need for the treatment head to be functional independent of these changing conditions.

Derived from this, and in a further preferred embodiment of the invention, the treatment head is adapted for immediate access to the body tissue on the inner circumferential tissue surface, while the treatment head is made of a material having a first refractive index of ≥1.64, in particular of ≥1.75. "Immediate access to the body tissue" means in the present context, that between the treatment head and the body tissue no optically relevant system elements like the aforementioned protective sleeve are present, and that the treatment head is exposed unprotected to the treatment site including the accompanying media like water and/or blood.

By choosing a treatment head material having a first refractive index of ≥1.64, an optimal half opening angle $\alpha_{opt}$ for use in air can be generated, which still provides total reflection in water with only minor deviations from the optimal 90° emerging direction. Such treatment head can be used both in air and water. By choosing a treatment head material having a first refractive index of >1.75, an optimal half opening angle $\alpha_{opt}$ for use in air can be generated, which still provides total reflection both in water and/or blood with only minor deviations from the optimal 90° emerging direction. Such treatment head can be used in air, water and blood. Both of the aforementioned treatment heads are in particular suitable for non-ablative tissue treatment, in particular in connection with a low water absorption laser wavelength, as generated e.g. by a Nd:YAG laser source.

The situation can be quite different when the treatment is performed with a wavelength which is highly absorbed in OH-containing liquids. There are currently three medical laser technologies, namely Er:YAG, Er:YSGG (or Er,Cr:YSGG), and $CO_2$, whose laser wavelengths operate in the same regions as the major absorption peaks for water. Since blood consists of 90% water, the skin consists of 70% water, and bone consists of 20% water, these three water-absorbed laser types are most suitable to be used for treating tissues according to the invention. But other laser sources may also be used, providing that their laser parameters are high enough to achieve tissue ablation.

Since the water-absorbed laser wavelengths are absorbed in blood and water within the penetration depth of a few micrometers, at first glance these types of lasers do not appear to be appropriate for treating tissues according to the invention when the surrounding media is an OH-containing liquid. Namely, a laser beam at a water-absorbed wavelength is expected to become absorbed immediately upon refracting out of the treatment head, which would prevent the laser beam from effectively reaching the circumferential tissue surface.

However, as experiments have shown, at sufficiently high intensities of the water-absorbed laser beam, a water vapor bubble channel is formed immediately upon the laser light exiting the treatment head and entering the water, effectively facilitating propagation of a water-absorbed laser light through water over relatively very long distances. In one experiment, an Er:YAG laser (2,940 nm) was used that has a pulse duration of 100 microseconds and a beam spot diameter of approximately 0.5 mm at the treatment's head cone. The treatment head was made out of a cylindrically shaped YAG crystal (diameter of 3 mm), ending with a conical tip with a cone angle of $\alpha=36'$. At pulse energies above approximately 100 mJ, up to 1 cm lone bubble channels were observed to be formed in water, in the perpendicular direction relative to the longitudinal axis of the YAG treatment head.

The phenomenon of bubble channel creation changes the conditions under which the treatment head is designed optimally for practicing the invention with water-absorbed laser wavelengths. The critical angle must be calculated assuming the presence of water or blood, while the optimal angle must be calculated for the case of a water vapor, with index of refraction approximately equal to $n_1=1$. It follows from Table 1 that for YAG the optimal angle in air of 36° fulfills also the condition for total internal reflection in water, and also in blood.

Derived from the aforementioned inventive considerations, and in a further preferred embodiment of the invention, the laser source is selected from an Er:YAG, an Er:YSGG, an Er,Cr:YSGG, and a $CO_2$ laser source, while the control device is adapted to control the laser source and the scanner such that the emerging beam section has on the conically shaped output surface a fluence of at least 1.0 $J/cm^2$. Besides the aforementioned pulse energy levels, it is said minimum fluence in connection with the laser energy absorption in water which causes the desired generation of bubble channels. Such laser system is in particular useful for an ablative tissue treatment.

In another preferred embodiment of the invention. the treatment head is made of YAG, while the half opening angle of the conically shaped output surface is in a range from 33°, inclusive, to 39°, inclusive, and is in particular 36°. Such treatment head can be used in any condition, regardless of the required and chosen laser wavelength, energy and/or fluence level, regardless of ablative or non-ablative treatment, and regardless of the presence of air, water and/or blood. Said treatment head provides an optimal, or close to optimal, half opening angle for air as a surrounding medium, while still providing total reflection in water and/or blood with only minor deviations from the optimal 90° emerging direction.

The inventive conically shaped output surface might be a truncated cone defined by its half opening angle, its maximum surface radius and its minimum surface radius being >0. In such a case, a bottom surface would be present, which is not irradiated and therefore passive in an optical sense. Only the truncated conically shaped output surface would be irradiated by the incoming beam section for total reflection and would be used for the subsequent refraction. In such a case, due to the minimum surface radius being >0, a laser energy overload of the treatment head can be easily avoided. However, in a further preferred embodiment the conically shaped output surface extends to the apex thereby featuring a minimum surface radius=0, and thereby forming a fully developed cone. This allows for an irradiation close to the apex, thereby achieving the maximum possible scanning distance in the radial and axial direction.

BRIEF DESCRIPTION OF THE DRAWINGS

An example of the inventive device and method will be explained in the following in more detail referring to the drawings.

DESCRIPTION OF PREFERRED EMBODIMENTS

Figure 1:
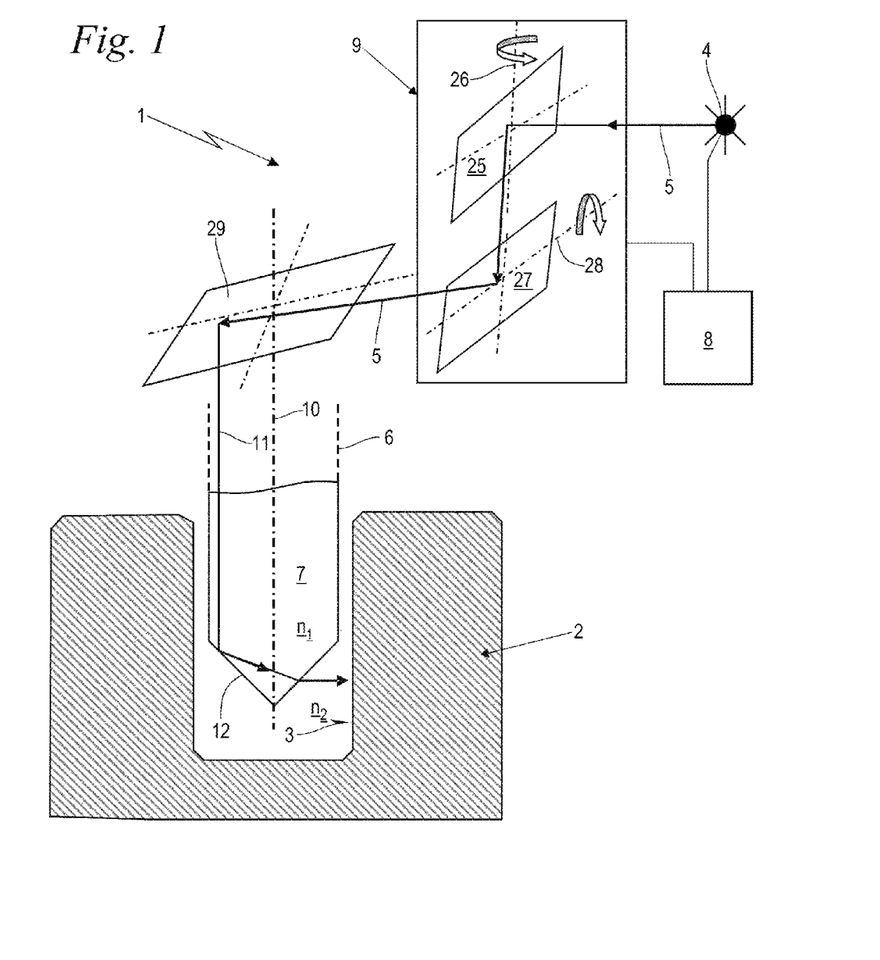
FIG. 1 shows a schematic cross sectional view of a body cavity with an inserted inventive treatment head providing total reflection followed by refraction of the laser beam at a conically shaped output surface of the treatment head.

FIG. 1 shows in a schematic cross sectional view a cavity in body tissue 2, wherein said cavity forms an inner circumferential tissue surface 3. For the treatment of the body tissue 2 on the inner circumferential tissue surface 3 an inventive laser system 1 and related inventive operation method is provided. The inventive laser system 1 is depicted in a schematic block diagram.

The laser system 1 comprises a laser source 4 for the generation of laser beam 5, a hand piece 6 with a treatment head 7, a control device 8, and a scanner 9. The scanner 9 comprises two mirrors 24, 27, which are rotationally movable about two perpendicular axes 26, 28. The rotational movement of both mirrors 25, 27 is controlled by the control device 8. Alternatively, the scanner 9 may comprise of only one mirror, 25 or 27, which is rotationally movable about two perpendicular axes. The control device 8 further controls the operation of the laser source 4 in terms of intensity and pulse sequences. Upon entering the scanner 9, the laser beam 5 subsequently impinges on both mirrors 25, 27, and is afterwards deflected by an optional bending mirror 29 such that the laser beam 5 enters the treatment head 7 of the hand piece 6 from an input side generally parallel to a longitudinal axis 10 along which the treatment head 7 extends. The portion of the laser beam 5 entering the treatment head 7 generally parallel to the longitudinal axis 10 defines an incoming beam section 11. In the shown embodiment, the incoming beam section 11 that is disposed generally parallel to the longitudinal axis 10 has its origin at the optional bending mirror 29. However, said origin may be located at the scanner 9 in case that the scanner 9 is directly disposed on the input side of the treatment head 7 and the longitudinal axis 10. In any case, the origin of the incoming beam section 11 is located at the input side of the treatment head 7. By controlling the rotational position of both mirrors 25, 27, the exact position of the laser beam's 5 incoming beam section 11 within the treatment head 7 relative to the longitudinal axis 10 can be adjusted. "Generally parallel" means in the present context that a mean course of the incoming beam section 11 is parallel to the longitudinal axis 10 and that the deviations from said parallelism as caused by the scanning action of the scanner 9 are included. The rigid treatment head 7 is made of a solid material which is transparent to the laser beam 5, having a laser beam transmission within the treatment head beam path length above 80%. On its free or distal end, the treatment head 7 has a conically shaped output surface 12 which provides a total reflection of the laser beam 5 followed by a subsequent refraction such that the laser beam 5 emerges from the treatment head 7 substantially radial to the longitudinal axis 10. In operation, the treatment head 7 is inserted into the body cavity such that the longitudinal axis 10 is substantially parallel to the inner tissue surface 3. In consequence, the emerging laser beam 5 impinges on the inner circumferential tissue 3 substantially perpendicular.

Figure 2:
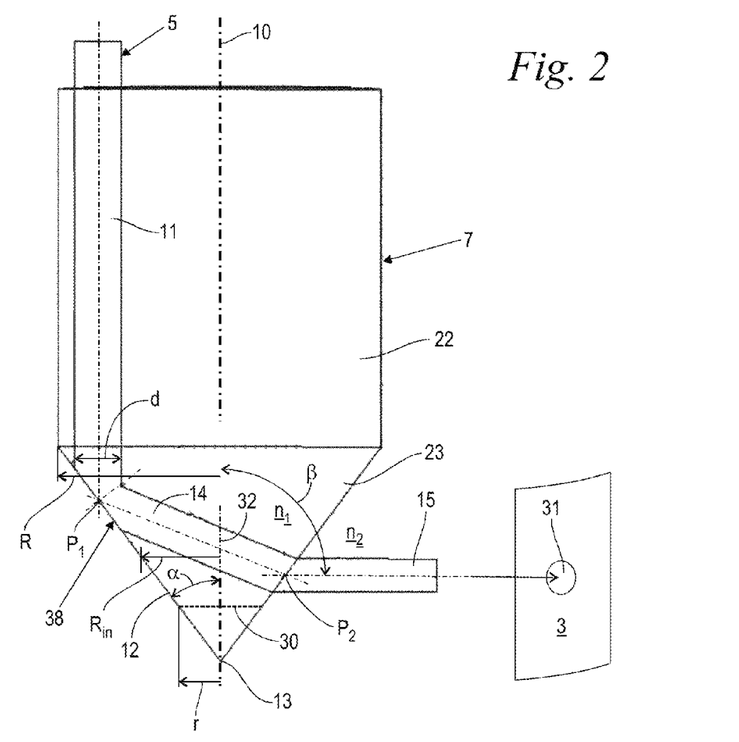
FIG. 2 shows an enlarged view of the treatment head of FIG. 1 with details of its geometric layout and the resulting laser beam path.

FIG. 2 shows in an enlarged schematic view the treatment head 7 according to FIG. 1 with details of its geometric layout and the resulting laser beam path. The rigid, solid and massive treatment head 7 comprises a base body 22 and an output body 23, which form a unitary one-piece (monolithic) construction. The base body 22 is cylindrically shaped. However, any other suitable shape with a longitudinal extension may be useful as well. The output body 23 is conically shaped with its cone base adjacent to the base body 22 and its apex 13 facing away from both the base body 22 and the origin of the incoming beam section 11, while the apex 13 is positioned on the longitudinal axis 10. Thereby, the conically shaped output surface 12 is formed on the output body 23.

At the cone base adjacent to the base body 22, the conically shaped output surface 12 has a maximum surface radius R corresponding to the radius of the base body 22. The conical output body 23 could be a truncated cone with a bottom 30 facing away from the base body 22, as schematically indicated by a dotted line. At the location of the bottom 30, the conically shaped output surface 12 has a minimum surface radius r. Both maximum and minimum surface radii R, r are measured perpendicular and relative to the longitudinal axis 10. In the shown longitudinal section, the conically shaped output surface 12 extends from the minimum surface radius r to the maximum surface radius R. In other words, any point on the output surface 12 has a local radius relative to the longitudinal axis 10 that is ≥the minimum surface radius r and ≤the maximum surface radius R. In the circumferential direction, the output surface 12 preferably extends 360° about the longitudinal axis 10. For certain applications however, a circumferential extension of less than 360° might be advisable within the scope of the invention. In the shown preferred embodiment, the conically shaped output surface 12 extends from the base body 22 to the apex 13 resulting in a minimum surface radius r=0. The geometric layout of the conically shaped output surface 12 is further defined by a half opening angle α relative to the longitudinal axis 10. A further optical property of the treatment head is a first refractive index $n_1$ of the material from which the treatment head 7 is made. As can be seen in both FIGS. 1 and 2, the treatment head 7 is used in a surrounding environment medium having a second refractive index $n_2$.

From the minimum surface radius r and the half opening angle α, a minimum scanning radius $R_{in}$ is derived based on Eq. 1. From the fact that the conically shaped output surface 12 has an apex facing away from the origin of the incoming beam section 11, it follows and is required that the minimum scanning radius $R_{in}$ is <the maximum surface radius R. A specific part or portion of the conically shaped output surface 12, which extends from the minimum scanning radius $R_{in}$ to the maximum surface radius R, is defined as a conically shaped scanning surface 38. In other words, any point on the scanning surface 38 has a local radius relative to the longitudinal axis 10 being ≥the minimum scanning radius $R_{in}$ and ≤the maximum surface radius R.

In operation, the laser beam 5 enters the treatment head 7 from the treatment head's 7 input side as said incoming beam section 11. The incoming beam section 11 first impinges with its centerline on the output surface 12 at a point $P_1$. At said first impingement point $P_1$, the incoming beam section 11 is totally reflected on the output surface 12, thereby forming a reflected beam section 14 crossing the longitudinal axis 10 within the output body 23 of the treatment head 7. At the location of total reflection the inventive laser system and method meet three requirements: Firstly, the incoming beam section 11 is adjusted to have at the location of the output surface 12, specifically at the first impingement point $P_1$, a mean beam diameter d being ≤the difference of the maximum surface radius R and the minimum scanning radius $R_{in}$. Secondly, the scanner 9 is controlled such that the incoming beam section 11 impinges on the first impingement point $P_1$ within the conically shaped scanning surface 38. Thirdly, the scanner 9 is controlled such that the first impingement point $P_1$ has sufficient distance to both the maximum surface radius R and the minimum scanning radius $R_{in}$ for providing total reflection of the incoming beam section 11 substantially throughout its entire mean beam diameter d. In other words, measured in the radial direction relative to the longitudinal axis, the first impingement point $P_1$ has a radial distance to both the maximum surface radius R and the minimum scanning radius $R_{in}$ substantially ≥half of the mean beam diameter d.

After crossing the longitudinal axis 10, the reflected beam section 14 of the laser beam 5 impinges again on the conically shaped output surface 12 on a point $P_2$ lying opposite the first impingement point $P_1$ relative to the longitudinal axis 10. At said second impingement point $P_2$, the reflected beam section 14 passes the output surface 12 to the outside of the treatment head 7, thereby being refracted into an emerging beam section 15 of the laser beam 5. By meeting the above mentioned three requirements at the location of total reflection, the scanning pattern is limited to a ring-shaped area, defined by an outer ring radius which is equal to the maximum surface radius R and an inner ring radius $R_{in}$ which can be mathematically calculated from Eq. 1. Thereby it is made sure, that the reflected beam section 14 is refracted into the emerging beam section 15 throughout its entire beam diameter or cross section, without irradiation the apex 13 or the bottom 30, if present, and without emitting a significant portion of, or even the entire, laser energy in the longitudinal direction. The emerging beam section 15 emerges radially from the treatment head 7, i.e. at an angle β of 90° with a tolerance of ±10°, preferably with a tolerance of ±3° relative to the longitudinal axis 10.

Figure 3:
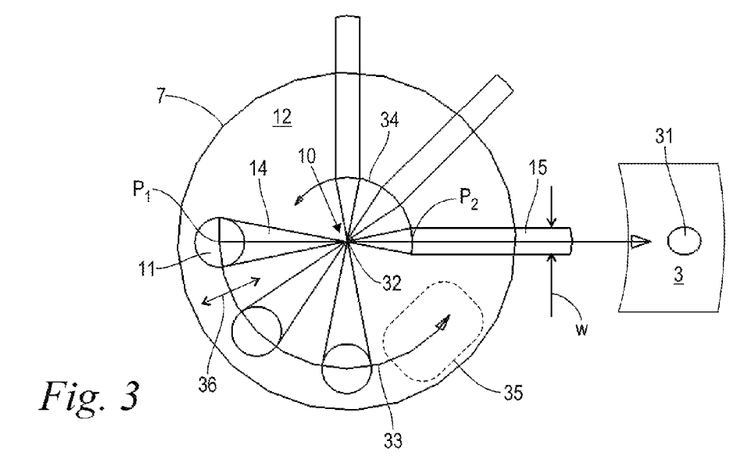
FIG. 3 shows a schematic top view of the treatment head of FIG. 1 with details of the related scanning pattern.

FIG. 3 shows in a schematic cross sectional top view the arrangement of FIG. 2. It can be seen that, due to the curvature of the output surface 12, the reflected beam section 14 is focussed onto the longitudinal axis 10. On the other hand, as shown in the side view of FIG. 2, the beam height of the reflected beam section 14 remains constant within the treatment head 7. As a result, the reflected beams section 14 forms a focal line 32 being disposed on the longitudinal axis 10. After having crossed the focal line 32, the beam width of the reflected beam section 14 widens again until reaching the second impingement point $P_2$, as shown in FIG. 3. Since said second impingement point $P_2$ is closer to the longitudinal axis 10 and the focal line 32 compared to the first impingement point $P_1$, the emerging beam section 15 has a beam width w being smaller than the beam diameter d of the incoming beam section 11 (FIG. 2). As a result, the emerging beam section 15 meets the circumferential tissue surface 3 in the form of an elliptical laser spot 31. The closer the second impingement point $P_2$ is disposed to the longitudinal axis 10 or the apex 13, the smaller the beam width w will be, resulting in an increased laser intensity and fluence. It is to be appreciated that FIG. 3 depicts what happens with a water-absorbed laser beam, where a water vapor bubble channel is formed immediately upon the laser light exiting the treatment head and entering the water, effectively facilitating propagation of a water-absorbed laser light through water over relatively very long distances without any significant broadening of the beam diameter. In order to avoid laser energy overload of the material of the treatment head 7, scanning of the conical output surface 12 is further desired such that a certain radial distance between both impingement points $P_1$, $P_2$ and between the first impingement point $P_1$ and the apex 13 is maintained such that the immediate vicinity of the apex 13 is excluded from irradiation by the reflected beam section 14.

Furthermore, according to the invention, a certain scanning pattern is performed by the scanner 9 and the control device 8 (FIG. 1), as shown in FIG. 3: According to the treatment requirements, the conical output surface 12 is scanned by the incoming beam section 11 on circles around the longitudinal axis 10 of the treatment head 7, as indicated by arrow 33, such that the emerging beam section 15 is subjected to a circular feed about the longitudinal axis 10, as indicated by arrow 34. Alternatively, the conically shaped output surface 12 is scanned by the incoming beam section 11 in a radial direction relative to the longitudinal axis 10, as indicated by arrow 36, as a consequence of which the emerging beam section 15 is subjected to an axial feed parallel to the direction of the longitudinal axis 10. Both circular and radial scanning patterns may be combined.

Scanning can be performed continuously or in the form of a discrete dot pattern. The dot pattern might be a regular one or a random one. For certain applications it is advisable to scan the output surface 12 such that at least one certain and predefined portion 35 of the output surface 12 is excluded from irradiation or is subjected to reduced irradiation intensity by the incoming beam section 11, which can be controlled by the control device 8 (FIG. 1). This results in a skipped or reduced irradiation of a certain portion of the tissue surface 3; this might be required e.g. in a vaginal treatment for protecting the urethra.

In order to achieve the described path of the laser beam 5 including the incoming beam section 11, the reflected beam section 14 and the emerging beam section 15 of the invention require a certain half opening angle α of the conically shaped output surface 12 adapted to the first refractive index $n_1$ of the treatment heads 7 material and the second refractive index $n_2$ of the medium immediately surrounding the output surface 12 of the treatment head 7. The adjustment of the half opening angle α is performed by meeting both aforementioned equations 1 and 2, thereby adjusting the half opening angle α to be at least approximately equal to the optimal angle $α_{opt}$. Dependent on the required application, the adjustment of the half opening angle α can be based on any surrounding medium having a second refractive index $n_2$. However, preferably a half opening angle α is chosen based on a second refractive index $n_2=1.0$. As long as it is made sure that such treatment head 7 is operated in air only having such second refractive index $n_2=1.0$, any optical material for forming the treatment head 7 having a first refractive index $n_1>1.28$ will allow for adjusting the half opening angle α to be the optimum angle $α_{opt}$. However, in case that the conically shaped output surface 12 come into contact with other media like water and/or blood, the conditions for total reflection and subsequent 90° refraction might not be met. In such cases, a treatment head material is chosen having a first refractive index $n_1 \geq 1.64$ for working in contact with water, or even having a first refraction $n_1 \geq 1.75$ for working in contact with water and/or blood.

Preferably, the treatment head 7 is made of YAG having a first refractive index $n_1$ of approximately 1.8, while the half opening angle α is in a range from 33°, inclusive, to 39°, inclusive, and is in particular 36° as shown in FIG. 2. Said half opening angle α=36° is equal to the optimal angle $α_{opt}$ as derived from both aforementioned equations 2 and 3, resulting in an angle β=90° when immersed in air having a second refractive index $n_2=1.0$, as shown in FIG. 2. In case of contact with water and/or blood the conditions for total reflection at the first impingement point $P_1$ are maintained, while the refraction at the second impingement point $P_2$ leads to an angle β only slightly deviating from the preferred 90° angle within the aforementioned tolerances. The half opening angle α of 36° as a preferred example, based on aforementioned equation 1, leads to a minimum scanning radius $R_{in}$ being 1.62× the minimum surface radius r.

The first preferred embodiment according to FIGS. 1, 2 and 3 is adapted for and used in immediate access to the body tissue 2 on the inner circumferential tissue surface 3. This means that no protection of the output surface 12 against treatment site media having the second refractive index $n_2$ is provided and that the output surface 12 might come into contact with said media.

In a first scenario, such laser system 1 including its treatment head 7 might be used for a non-ablative treatment of the tissue surface 3. In such case, the laser source 4 is chosen to provide a wavelength of the laser beam 5 which is not much absorbed by water. Preferably, the laser source 4 is a Nd:YAG laser source providing a laser beam 5 with a wavelength of 1,064 nm. Such laser beam 5 passes from the treatment head 7 to the tissue surface 3 even in cases when the medium in between is water and/or blood. Any desired laser parameters like pulse sequences, pulse durations, energy levels, and fluences can be chosen to perform the desired non-ablative treatment of the tissue surface 3.

In an alternative scenario, an ablative treatment of the tissue surface 3 might be required. In such cases, a laser source 4 is chosen to provide a laser beam 5 having a strongly water-absorbable wavelength. Preferably, such laser source is selected from an Er:YAG, an Er:YSGG, an Er,Cr:YSGG, and a $CO_2$ laser source. In case of air being the surrounding medium, such laser beam 5 reaches unhindered the tissue surface 3. In case of water and/or blood being the surrounding medium, the water content absorbs a significant amount of the laser energy when emerging from the output surface 12. In such cases, it is preferable to control the laser source 4 and the scanner 9 by means of the control device 8 such that the emerging beam section 15 has at the second impingement point $P_2$ of the conically shaped output 12 a fluence of at least 1.0 J/cm². By applying such a fluence level, the emerging beam section 15 causes vaporisation of the water containing surrounding medium. Thereby a so-called tunneling effect is achieved, by which the emerging beam section 5 passes through vapour bubbles to the tissue surface 3 as required.

The shown embodiment can be used for post treatment of drilling holes in hard bone material e.g. in implantology. In such a case, the treatment head 7 preferably has a diameter in a range from 2.0 mm to 6.0 mm corresponding to a maximum surface radius R in a range from 1.0 mm to 3.0 mm. The preferred laser source 4 is an Er:YAG laser source being operated in a pulse mode with pulse durations in a range from 10 µs to 1,000 µs, with pulse energies in a range from 5 mJ to 2,000 mJ, and with mean diameters of the laser spots 31 in a range from 0.2 mm to 1.5 mm.

The shown embodiment can also be used for thermally treating soft tissue in body cavities such as vagina and anus. In gynecology, the method and device can be used to treat stress and mixed stress urinary incontinence, vaginal atrophy, and vaginal relaxation syndrome. In such cases the treatment head 7 preferably has a diameter in a range from 8.0 mm to 50.0 mm corresponding to a maximum surface radius R in a range from 4.0 mm to 25.0 mm. The preferred laser source 4 is an Er:YAG laser source being operated in a pulse mode with pulse duration, in a range from 10 µs to 2,000 µs, with pulse energies in a range from 5 mJ to 2,000 mJ, and with mean diameters of the laser spots 31 in a range from 0.2 mm to 20 mm.

Figure 4:
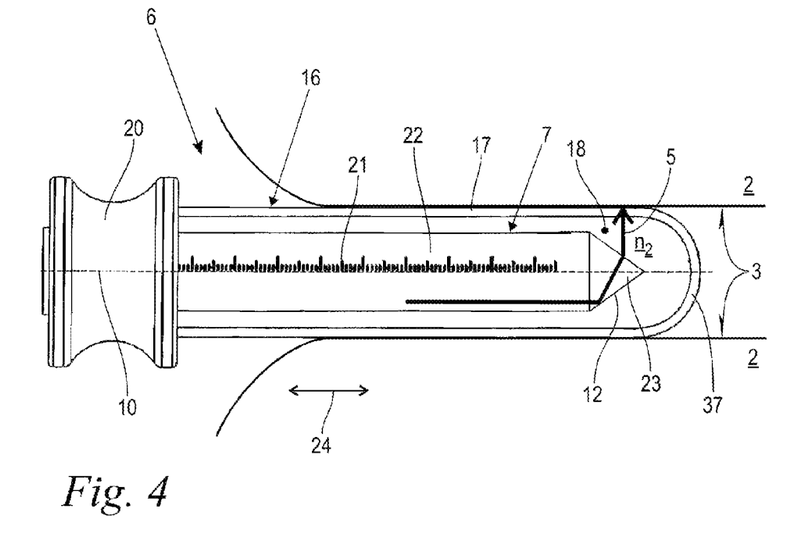
FIG. 4 is a schematic cross sectional side view of the treatment head of FIG. 1 surrounded by a protective sleeve.

FIG. 4 shows in a schematic cross-sectional side view a second preferred embodiment of the inventive hand piece 6 as part of the laser system 1 according to FIG. 1. The hand piece 6 comprises a grip 20 for manual movement, to which the treatment head 7 is attached. Unless explicitly mentioned otherwise, the treatment head 7 is identical to the treatment head 7 according to FIGS. 1, 2 and 3. The hand piece 6 further comprises a liquid-tight protective sleeve 16, which is attached to the grip 20 and which entirely covers the treatment head 7. The liquid-tight protective sleeve 16 is made of a material transparent to the laser beam 5 and comprises a circumferential wall 17, which is closed at its free distal end by a spherical end portion 37. The circumferential wall 17 is generally cylindrically shaped. However, any other longitudinally extending shape with e.g. a polygonal cross section might be usable as well. The circumferential wall 17 extends in the direction of the longitudinal axis 10 across the output body 23 of the treatment head 7, thereby leaving a free space 18 between the conically shaped output surface 12 at the circumferential wall 17. The free space 18 is filled with gas, preferably with air. However, any other gas fill or even a vacuum will do, as long as the medium within the free space 18 has a second refractive index $n_2$ that is at least approximately 1.0.

The hand piece 6 is inserted with its treatment head 7 and its surrounding protective sleeve 16 into a schematically sketched woman's vagina for treatment of the inner circumferential tissue surface 3 of the body mucosa tissue 2. The entire treatment head 7 including its conically shaped output surface 12 is shielded from any treatment site's water-containing and/or blood-containing liquid by means of the protective sleeve 16. Total reflection and refraction conditions of the laser beam 5 are maintained under the conditions of a surrounding medium having a second refractive index $n_2$ of approximately 1.0. After emerging from the output body 23, the laser beam 5 passes unhindered through the free space 18 and the circumferential wall 17, until it reaches the target site on the tissue surface 3.

On the outer surface of the treatment head 7 a depth scale 21 is provided, which allows for an exact axial positioning of the handpiece 6 relative to the treatment site. Said optional depth scale 21 may be incorporated into the embodiment according to FIGS. 1, 2, and 3 as well. In the embodiment of FIG. 4 the depth scale 21 may be alternatively positioned on the outer surface of the protective sleeve 16.

The hand piece 6 according to FIG. 4 is part of a laser system 1 as described with the aid of FIGS. 1, 2, and 3. All related features and process steps may be applied with the hand piece 6 of FIG. 4. However, since the protective sleeve 16 allows for excluding the optical influence of water, blood and other surrounding media, any desired treatment process can be applied. This includes both ablative and non-ablative treatments with any suitable laser beam wavelength, fluence and energy levels, pulse sequences and so forth. The treatment of the vagina as disclosed is an exemplary non-limiting embodiment only. Any other circumferential tissue surface 3 of a body opening can be treated including urinal, rectal, ENT (ear, nose and throat) and implantology applications.

The specification incorporates by reference the entire disclosure of European priority document EP 13 003 273.3 having a filing date of Jun. 27, 2013.

While specific embodiments of the invention have been shown and described in detail to illustrate the inventive principles, it will be understood that the invention may be embodied otherwise without departing from such principles.

What is claimed is:

1. A laser system (1) for the treatment of body tissue (2) on an inner circumferential tissue surface (3), the laser system comprising:
   a laser source (4) adapted to generate a laser beam (5),
   a handpiece (6) with a treatment head (7),
   a control device (8), and
   a scanner (9),
   wherein the treatment head (7) extends along a longitudinal axis (10) and is made of a material transparent to the laser beam (5) and has a first refractive index,
   wherein, during operation of the laser system, an incoming beam section (11) of the laser beam (5) enters the treatment head (7) in a direction of the longitudinal axis (10),
   wherein the treatment head (7) has a conically shaped output surface (12) disposed around the longitudinal axis (10) and having an apex (13) facing away from an origin of the incoming beam section (11),
   wherein the conically shaped output surface (12) has a minimum surface radius (r) and a maximum surface radius (R),
   wherein the conically shaped output surface (12) has a half opening angle (α) adapted to provide total reflection of the incoming beam section (11) into a reflected beam section (14) within the treatment head (7) and adapted to provide refraction of the reflected beam section (14) into an emerging beam section (15) emerging radially from the treatment head (7) through the output surface (12),
   wherein a minimum scanning radius ($R_{in}$) is derived from the minimum surface radius (r) and the half opening angle (α) according to:

$$R_{in}=r(tg(2\alpha)+tg(\alpha))/(tg(2\alpha)-tg(\alpha)),$$

wherein the incoming beam section (11) has at the location of the output surface (12) a mean diameter (d) that is ≤a difference of the maximum surface radius (R) and the minimum scanning radius ($R_{in}$), wherein, as a part of the conically shaped output surface (12), a conically shaped scanning surface (38) is defined extending from the minimum scanning radius ($R_{in}$) to the maximum surface radius (R), wherein the control device (8) is adapted to control the scanner (9) for scanning at least a portion of the conically shaped scanning surface (38) with the incoming beam section (11).

2. The laser system according to claim 1, wherein the first refractive index of the material of the treatment head (7) is >1.28, wherein air surrounding the treatment head (7) has a second refractive index of 1.0, wherein an optimal half opening angle ($\alpha_{opt}$) of the conically shaped output surface (12) is derived from the first refractive index and the second refractive index, and wherein the half opening angle ($\alpha$) of the conically shaped output surface (12) is at least approximately equal to the optimal half opening angle ($\alpha_{opt}$).

3. The laser system according to claim 1, further comprising a liquid-tight protective sleeve (16) that covers the treatment head (7) and is made of a material that is transparent to the laser beam (5), wherein the conically shaped output surface (12) is surrounded by a circumferential wall (17) of the protective sleeve (16), and wherein a free space (18) between the conically shaped output surface (12) and the circumferential wall (17) is filled with gas.

4. The laser system according to claim 1, wherein the treatment head (7) is adapted for immediate access to the body tissue (2) on the inner circumferential tissue surface (3), and wherein the first refractive index of the material of the treatment head (7) >1.64.

5. The laser system according to claim 4, wherein the laser source (4) is selected from the group consisting of an Er:YAG laser source, an Er:YSGG laser source, an Er,Cr:YSGG laser source, and a $CO_2$ laser source, and wherein the control device (8) is adapted to control the laser source (4) and the scanner (9) such that the emerging beam section (15) has a fluence of at least 1.0 $J/cm^2$ at the conically shaped output surface (12).

6. The laser system according to claim 1, wherein the material of the treatment head (7) is YAG, and wherein the half opening angle ($\alpha$) of the conically shaped output surface (12) is in a range from 33° to 39°, with 33° and 39° included in the range.

7. The laser system according to claim 1, wherein the conically shaped output surface (12) extends to the apex (13) and has a minimum surface radius (r)=0.

8. The laser system according to claim 1, wherein the material of the treatment head (7) has a laser beam transmission above 80% within a treatment head beam path length.

9. The laser system according to claim 1, wherein the control device (8) is adapted to control scanning of the conically shaped output surface (12) by the incoming beam section (11) of the laser beam (5) on circles around the longitudinal axis (10) of the treatment head (7) such that the emerging beam section (15) is subjected to a circular feed about the longitudinal axis (10).

10. The laser system according to claim 1, wherein the control device (8) is adapted to control scanning of the conically shaped output surface (12) by the incoming beam section (11) of the laser beam (5) in a radial direction relative to the longitudinal axis (10) of the treatment head (7) such that the emerging beam section (15) is subjected to an axial feed parallel to the direction of the longitudinal axis (10).

11. The laser system according to claim 1, wherein the control device (8) is adapted to control scanning of the conically shaped output surface (12) by the incoming beam section (11) of the laser beam (5) in a random pattern.

12. The laser system according to claim 1, wherein the control device (8) is adapted to control scanning of the conically shaped output surface (12) by the incoming beam section (11) of the laser beam (5) such that at least one certain and predefined portion (35) of the output surface (12) is excluded from irradiation or is subjected to a reduced irradiation by the incoming beam section (11).

13. A method for operating a laser system (1) for the treatment of body tissue (2) on an inner circumferential tissue surface (3), wherein the laser system (1) comprises:
a laser source (4) adapted to generate a laser beam (5),
a handpiece (6) with a treatment head (7),
a control device (8), and
a scanner (9),
wherein the treatment head (7) extends along a longitudinal axis (10) and is made of a material transparent to the laser beam (5) and has a first refractive index,
wherein, during operation of the laser system, an incoming beam section (11) of the laser beam (5) enters the treatment head (7) in a direction of the longitudinal axis (10),
wherein the treatment head (7) has a conically shaped output surface (12) disposed around the longitudinal axis (10) and having an apex (13) facing away from an origin of the incoming beam section (11),
wherein the conically shaped output surface (12) has a minimum surface radius (r) and a maximum surface radius (R),
wherein the conically shaped output surface (12) has a half opening angle ($\alpha$) adapted to provide total reflection of the incoming beam section (11) into a reflected beam section (14) within the treatment head (7) and adapted to provide refraction of the reflected beam section (14) into an emerging beam section (15) emerging radially from the treatment head (7) through the output surface (12),
wherein a minimum scanning radius ($R_{in}$) is derived from the minimum surface radius (r) and the half opening angle ($\alpha$) according to:

$$R_{in}=r(tg(2\alpha)+tg(\alpha))/(tg(2\alpha)-tg(\alpha)),$$

wherein the incoming beam section (11) has at the location of the output surface (12) a mean diameter (d) that is ≤a difference of the maximum surface radius (R) and the minimum scanning radius ($R_{in}$),
wherein, as a part of the conically shaped output surface (12), a conically shaped scanning surface (38) is defined extending from the minimum scanning radius ($R_{in}$) to the maximum surface radius (R), the method comprising:
positioning during operation of the laser system (1) the longitudinal axis (10) of the treatment head (7) at least approximately parallel to the inner circumferential tissue surface (3),
controlling with the control device (8) the scanner (9) to scan at least a portion of the conically shaped scanning surface (38) with the incoming beam section (11) such that:

the incoming beam section (11) is subjected to total reflection at the conically shaped scanning surface (38) into a reflected beam section (14) within the treatment head (7), and the reflected beam section (14) is refracted at the conically shaped output surface (12) into an emerging beam section (15) radially emerging from the treatment head (7) through the output surface (12), scanning the inner circumferential tissue surface (3) at least partially by the emerging beam section (15).

14. The method according to claim 13, wherein the inner circumferential tissue surface (3) of the body tissue (2) is accessed by the treatment head (7), the method further comprising:

selecting the material of the treatment head (7) to have a first refractive index of >1.28, covering the treatment head (7) with a liquid-tight protective sleeve (16) such that the conically shaped output surface (12) is surrounded by a circumferential wall (17) of the protective sleeve (16), filling a free space (18) between the conically shaped output surface (12) and the circumferential wall (y) with gas.

15. The method according to claim 13, wherein the inner circumferential tissue surface (3) of the body tissue (2) is immediately accessed by the treatment head (7), further comprising:

selecting the material of the treatment head (7) to have a first refractive index of >1.64, and using the treatment head (7) in an environment in which water is present.

16. The method according to claim 13, wherein the inner circumferential tissue surface (3) of the body tissue (2) is immediately accessed by the treatment head (7), further comprising:

selecting the material of the treatment head (7) to have a first refractive index of >1.75, and using the treatment head (7) in an environment in which blood is present.

17. The method according to claim 13, further comprising:

selecting the laser source from the group consisting of an Er:YAG laser source, an Er:YSGG laser source, an Er,Cr:YSGG laser source, and a $CO_2$ laser source, and applying parameters of the laser beam (5) to provide a fluence of the emerging beam section (15) at the conically shaped output surface (12) of at least 1.0 $J/cm^2$.

18. The method according to claim 13, wherein, in the step of controlling, the scanner (9) is controlled such that at least one certain and predefined portion of the circumferential tissue surface (3) is excluded from irradiation or is subjected to a reduced irradiation by the emerging beam section (15).

* * * * *